(12) United States Patent
De Crecy (10) Patent No.: US 9,428,734 B2
(45) Date of Patent: *Aug. 30, 2016

(54) CONTINUOUS CULTURE APPARATUS WITH MOBILE VESSEL, ALLOWING SELECTION OF FITTER CELL VARIANTS AND PRODUCING A CULTURE IN A CONTINUOUS MANNER

(71) Applicant: Eudes Francois Marie De Crecy, Gainesville, FL (US)

(72) Inventor: Eudes Francois Marie De Crecy, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/218,294

(22) Filed: Mar. 18, 2014

(65) Prior Publication Data

US 2015/0056644 A1  Feb. 26, 2015

Related U.S. Application Data

(63) Continuation of application No. 13/430,220, filed on Mar. 26, 2012, now abandoned, which is a continuation of application No. 11/508,286, filed on Aug. 23, 2006, now abandoned, which is a continuation-in-part of application No. PCT/US2005/005616, filed on Feb. 23, 2005.

(60) Provisional application No. 60/547,379, filed on Feb. 23, 2004.

(51) Int. Cl.
*C12M 1/00* (2006.01)
*C12M 3/00* (2006.01)
*C12N 5/077* (2010.01)
(Continued)

(52) U.S. Cl.
CPC ............ *C12N 5/0673* (2013.01); *C12M 23/06* (2013.01); *C12M 23/26* (2013.01); *C12M 23/34* (2013.01); *C12M 41/26* (2013.01); *C12M 41/36* (2013.01); *C12M 41/40* (2013.01); *C12N 1/16* (2013.01); *C12N 1/20* (2013.01); *C12N 5/04* (2013.01); *C12N 5/0605* (2013.01); *C12N 5/0606* (2013.01); *C12N 5/0622* (2013.01);
(Continued)

(58) Field of Classification Search
CPC .... C12M 23/06; C12M 23/26; C12M 23/34; C12M 41/26; C12M 41/36; C12M 41/40; C12N 1/16; C12N 1/20; C12N 5/04; C12N 5/0605; C12N 5/0606; C12N 5/0622; C12N 5/0647; C12N 5/0669; C12N 5/0673; C12N 7/00
USPC ............ 435/286.5, 289.1, 293.1, 298.2, 304, 435/29, 252.1, 235.1
See application file for complete search history.

(56) References Cited

U.S. PATENT DOCUMENTS 4,686,189 A   8/1987 Redikultsev et al.
4,703,010 A   10/1987 Yunker et al.
(Continued)

FOREIGN PATENT DOCUMENTS

CH   552063   7/1974
JP   03-030665   2/1991
(Continued)

OTHER PUBLICATIONS

University of California press (UC Press) E-book Collection, 1985-2004, pp. 403.
(Continued)

*Primary Examiner* — Michael Marcheschi
*Assistant Examiner* — Shanta G Doe
(74) *Attorney, Agent, or Firm* — Young & Thompson (57) ABSTRACT

A method and device for growing plant, animal or stem cells in a continuous manner.

21 Claims, 4 Drawing Sheets

(51) Int. Cl.

| | | |
|---|---|---|
| *C12M 1/12* | (2006.01) | |
| *C12M 1/34* | (2006.01) | |
| *C12N 1/16* | (2006.01) | |
| *C12N 1/20* | (2006.01) | |
| *C12N 5/04* | (2006.01) | |
| *C12N 5/073* | (2010.01) | |
| *C12N 5/0735* | (2010.01) | |
| *C12N 5/079* | (2010.01) | |
| *C12N 5/0789* | (2010.01) | |
| *C12N 7/00* | (2006.01) | |

(52) U.S. Cl.
CPC ........... *C12N5/0647* (2013.01); *C12N 5/0669* (2013.01); *C12N 7/00* (2013.01)

(56) References Cited

U.S. PATENT DOCUMENTS

| | | |
|---|---|---|
| 4,734,372 A | 3/1988 | Rotman |
| 5,071,760 A | 12/1991 | Watanabe et al. |
| 5,399,493 A | 3/1995 | Emerson et al. |
| 5,786,215 A | 7/1998 | Brown et al. |
| 6,403,369 B1 | 6/2002 | Wood |
| 6,537,772 B1 | 3/2003 | Alarcon et al. |
| 6,686,194 B1 | 2/2004 | Mutzel et al. |
| 7,939,315 B2 * | 5/2011 | De Crecy .............. C12M 23/06 435/292.1 |
| 2003/0235909 A1 | 12/2003 | Hariri et al. |
| 2004/0029265 A1 | 2/2004 | Doi et al. |

FOREIGN PATENT DOCUMENTS

| | | |
|---|---|---|
| JP | 2001-258545 | 9/2001 |
| JP | 2004-208663 | 7/2004 |

OTHER PUBLICATIONS

Machine translation of CH552063 which was published Jul. 1974.
Machine translation of JP H3-30665 which was published Feb. 1991.
Dykhuizen et al., Selection in Chemostats, Microbiology Reviews, Jun. 1983, vol. 47, pp. 150-160.
www. thefreedictionary.com doc. for natural selection.
www.thefreedictionary.com doc of adaptive evolution.

* cited by examiner

Fig. 3 - Tube full of medium before injection - Status T0. Fresh medium in every region of tubing A, B, C, D & E.

Fig. 4 - Chamber just after injection - Status T1, just at the beginning of first cycle. Culture growing in regions C & B.

Fig. 5 - Status T2, during first growth cycle. Culture growing in regions C & B.

Fig. 6 - Status T3, just at the beginning of second growth cycle, just after first tube movement. Culture growing in region D & C.

Fig. 7 - Status T4, during second growth cycle. Culture growing in regions D & C.

Fig. 8 - Status T5, just at the beginning of third growth cycle, just after second tube movement. Culture growing in regions E & D.

Fig. 9 - Status T6, during third growth cycle. Culture growing in regions E & D.

CONTINUOUS CULTURE APPARATUS WITH MOBILE VESSEL, ALLOWING SELECTION OF FITTER CELL VARIANTS AND PRODUCING A CULTURE IN A CONTINUOUS MANNER

CROSS REFERENCE TO RELATED APPLICATIONS

This application is a continuation of application Ser. No. 13/430,220 filed on Mar. 26, 2012, now abandoned, which is a continuation of application Ser. No. 11/508,286 filed on Aug. 23, 2006, now abandoned, which is a continuation-in-part of PCT/US2005/005616 filed on Feb. 23, 2005, which claims the benefit of 60/833,821 filed on Jul. 28, 2006. PCT/US2005/005616 filed on Feb. 23, 2005 claims the benefit of 60/547,379 filed on Feb. 23, 2004. The entire contents of each of these applications are hereby expressly incorporated by reference.

FIELD OF THE INVENTION

The described invention provides a method and a device that allow selection of living cells, with increased rates of reproduction and specific metabolic properties, in a liquid or semi-solid medium. For the process of selection (adaptive evolution), genetically variant organisms (mutants) arise in a population and compete with other variants of the same origin. Those with the fastest rate of reproduction increase in relative proportion over time, leading to a population (and individual organisms) with increased reproductive rate. This process can improve the performance of organisms used in industrial processes or academic purpose. The present invention utilizes a continuous culture apparatus to achieve the viable production of living cells, for example, yeast, plant cells, animal cells or stem cells. The present invention may be used to produce an active ingredient or biologic that is produced by the living cells. The active ingredient or biologic may in turn be used as a diagnostic, preventive, or therapeutic agent.

BACKGROUND OF THE INVENTION

Selection for increased reproductive rate (fitness) requires sustained growth, which is achieved through regular dilution of a growing culture. In the prior art this has been accomplished two ways: serial dilution and continuous culture, which differ primarily in the degree of dilution.

Serial culture involves repetitive transfer of a small volume of grown culture to a much larger vessel containing fresh growth medium. When the cultured cells have grown to saturation in the new vessel, the process is repeated. This method has been used to achieve the longest demonstrations of sustained culture in the literature (Lenski & Travisano: Dynamics of adaptation and diversification: a 10,000-generation experiment with bacterial populations. 1994. Proc Natl Acad Sci USA. 15:6808-14), in experiments which clearly demonstrated consistent improvement in reproductive rate over period of years. This process is usually done manually, with considerable labor investment, and is subject to contamination through exposure to the outside environment. Serial culture is also inefficient, as described in the following paragraph.

The rate of selection, or the rate of improvement in reproductive rate, is dependant on population size (Fisher: The Genetical Theory of Natural Selection. 1930. Oxford University Press, London, UK). Furthermore, in a situation like serial transfer where population size fluctuates rapidly, selection is proportional to the harmonic mean ($\tilde{N}$) of the population (Wright: Size of population and breeding structure in relation to evolution. 1938. Science 87: 430-431), and hence can be approximated by the lowest population during the cycle.

Population size can be sustained, and selection therefore made more efficient, through continuous culture. Continuous culture, as distinguished from serial dilution, involves smaller relative volume such that a small portion of a growing culture is regularly replaced by an equal volume of fresh growth medium. This process maximizes the effective population size by increasing its minimum size during cyclical dilution. Devices allowing continuous culture are termed "chemostats" if dilutions occur at specified time intervals, and "turbidostats" if dilution occur automatically when the culture grows to a specific density.

For the sake of simplicity, both types of devices will hereafter be grouped under the term "chemostat". Chemostats were invented simultaneously by two groups in the 1950's (Novick & Szilard: Description of the chemostat. 1950. Science 112: 715-716) and (Monod: La technique de la culture continue—Théorie et applications. 1950. Ann. Inst. Pasteur 79:390-410). Chemostats have been used to demonstrate short periods of rapid improvement in reproductive rate (Dykhuizen D E. Chemostats used for studying natural selection and adaptive evolution. 1993. Methods Enzymol. 224:613-31).

Traditional chemostats are unable to sustain long periods of selection for increased reproduction rate, due to the unintended selection of dilution-resistant (static) variants. These variants are able to resist dilution by adhering to the surface of the chemostat, and by doing so, outcompete less sticky individuals including those that have higher reproductive rates, thus obviating the intended purpose of the device (Chao & Ramsdell: The effects of wall populations on coexistence of bacteria in the liquid phase of chemostat cultures, 1985. J. Gen. Microbiol. 131: 1229-36).

One method and chemostatic device (the Genetic Engine) has been invented to avoid dilution resistance in continuous culture (U.S. Pat. No. 6,686,194-B1 filed by PASTEUR INSTITUT [FR] & MUTZEL RUPERT [DE]). This method uses valve controlled fluid transfer to periodically move the growing culture between two chemostats, allowing each to be sterilized and rinsed between periods of active culture growth. The regular sterilization cycles prevent selection of dilution-resistant variants by destroying them. This method and device achieves the goal, but requires independent complex manipulations of several fluids within a sterile (sealed) environment, including one (NaOH) which is both very caustic and potentially very reactive, quickly damaging valves, and posing containment and waste-disposal problems. The chemostatic device is also limited in that no provisions are made to provide a support for cells to grow on There are some types of cells that are difficult to culture in large amounts due to the conditions the cells require to survive and grow. It is believed that these cells could grow in conditions provided by a continuous culture approach. This is particularly the case for stem cells.

For example, human embryonic stem cells are typically grown by isolating and transferring a stem cell mass into a plastic laboratory culture dish that contains a nutrient broth known as culture medium. The cells divide and spread over the surface of the culture dish. The inner surface of the culture dish is typically coated with mouse embryonic skin cells that have been treated so they will not divide. This coating layer of cells is called a feeder layer. The reason for having the feeder layer in the bottom of the culture dish is to give the human embryonic stem cells a sticky surface to which they can attach. Also, the feeder cells release nutrients into the culture medium. Recently, scientists have begun to devise ways of growing embryonic stem cells without the mouse feeder cells. This is a significant scientific advancement because it avoids the risk that viruses or other macromolecules in the mouse cells may be transmitted to the human cells.

Over the course of several days, the cells of the inner cell mass proliferate and begin to crowd the culture dish. When this occurs, they are removed gently and plated into several fresh culture dishes. The process of replating the cells is repeated many times and for many months, and is called subculturing. Each cycle of subculturing the cells is referred to as a passage. After six months or more, the original cells of the cell mass yield millions of embryonic stem cells. Embryonic stem cells that have proliferated in cell culture for six or more months without differentiating, are pluripotent, and appear genetically normal are referred to as an embryonic stem cell line.

Once cell lines are established, or even before that stage, batches of them can be frozen and shipped to other laboratories for further culture and experimentation. However, continuous culture grants the advantage of suppressing a maximum of manipulations that stress the living cells and create a potential source of contamination. When a culture is started, continuous culture conditions allow the skilled artisan to take advantage of a continuous production of cells. Once stem cells are being produced, the production of stems cells could continue without interruption to produce substantially more stem cells than methods that are typically used today.

SUMMARY OF THE INVENTION

It is therefore an object of the present invention to provide an improved (and completely independent) method and device for continuous culture of cells (including bacteria, archaea, eukaryotes and viruses) without interference from dilution-resistant variants. Like other chemostats, the device provides a means for regular dilution of a grown culture with fresh growth medium, a means for gas exchange between the culture and the outside environment, sterility, and automatic operation as either a chemostat or a turbidostat.

Additionally, it is an object of the present invention to provide an improved and distinct method and device for continuous culture of cells such as plant cells, animal cells or stem cells. Stem cells that may be cultured with the present invention include but are not limited to embryonic stem cells, fetal stem cells, umbilical cord stem cells, placenta derived stem cells, and adult stem cells. The adult stem cells that may be cultured with the present invention include but are not limited to hematopoietic stem cells, bone marrow stem cells, stromal cells, astrocytes and oligidendrocytes (e.g, Hematopoietic Stem Cell Protocols by C. Klug and C. Jordan, Humana Press, Totowa, N.J., 2002, incorporated by reference herein).

The present invention is designed to achieve these goals without any fluid transfer, including sterilization or rinsing functions. This represents a specific advantage of the present invention with respect to prior art in so far as it avoids the hazards and difficulties associated with sterilization and rinsing, including containment and complex fluid transfers involving caustic solvents.

Continuous culture is achieved inside a flexible sterile tube filled with growth medium. The medium and the chamber surface are static with respect to each other, and both are regularly and simultaneously replaced by peristaltic movement of the tubing through "gates", or points at which the tube is sterilely subdivided by clamps that prevent the cultured cells from moving between regions of the tube. UV gates can also (optionally) be added upstream and downstream of the culture vessel for additional security.

The present method and device are also an improvement over prior art insofar as they continually, rather than periodically, select against adherence of dilution-resistant variants to the chemostat surfaces, as replacement of the affected surfaces occurs in tandem with the process of dilution.

The tube is subdivided in a transient way such that there are regions that contain saturated (fully grown) culture, regions that contain fresh medium, and a region between these two, wherein one or more chambers referred to as growth or culture chambers are present to form a growth chamber region in which grown culture is mixed with fresh medium to achieve dilution. The gates are periodically released from one point on the tube and replaced at another point, such that grown culture along with its associated growth chamber surface and attached static cells, is removed by isolation from the growth chamber and replaced by both fresh medium and fresh chamber surface.

BRIEF DESCRIPTION OF THE DRAWINGS

Without being exhaustive and limiting, one possible general configuration will include several components as described hereafter. In the following the present invention is exemplarily explained on the basis of a preferred embodiment, thereby referring to the drawings in which:

FIGS. 3 to 9 represents said flexible tubing (1) in place in said thermostatically controlled box (2) and introduced through gates (3), (4) and (5) through which said tubing will stay during all steps of process and through which said tubing will move according to its peristaltic movement.

DETAILED DESCRIPTION OF INVENTION

The basic operation of the device is depicted in FIGS. 3 through 9.

Figure 1:
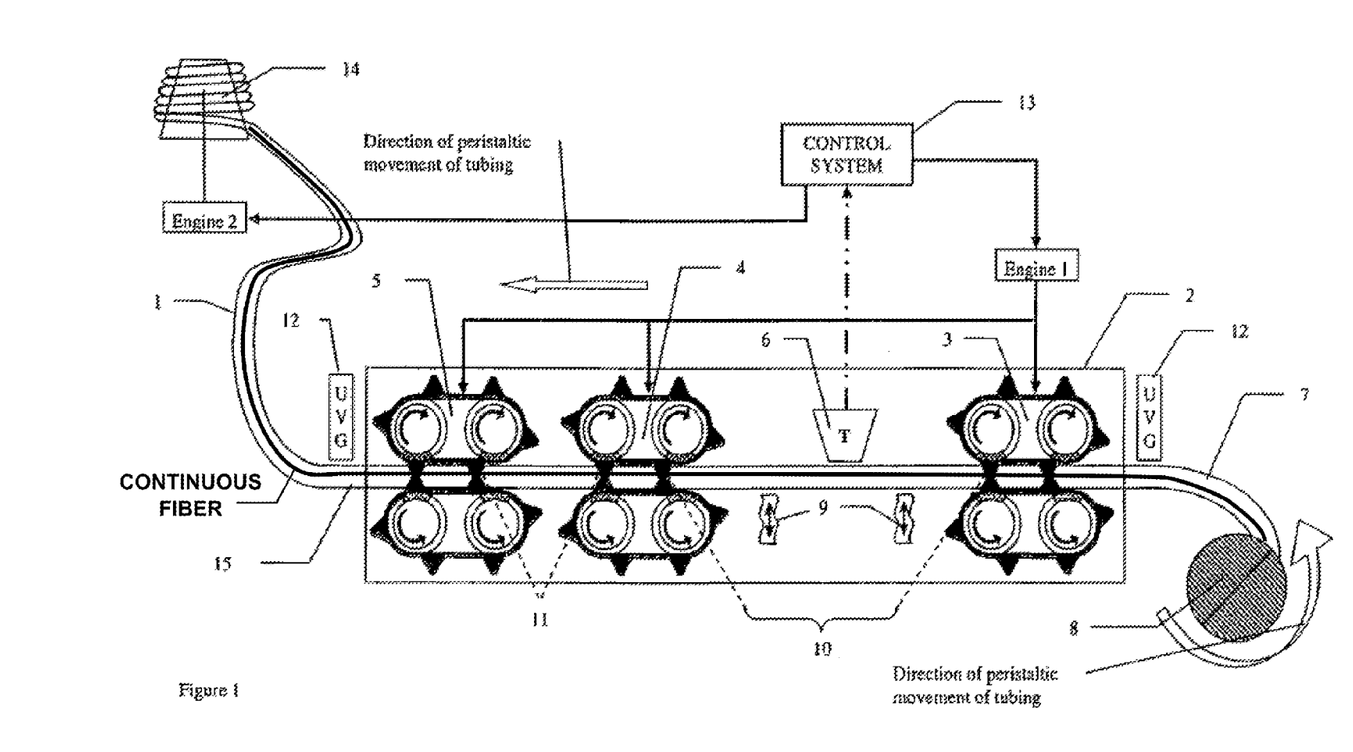
FIG. 1 displays an overall view of a possible configuration of the device in which:
(1) represents the flexible tubing containing the different regions of the device which are: upstream fresh medium (7), growth chamber (10), sampling chamber (11) and disposed grown culture region (15)
(2) represents the thermostatically controlled box allowing regulation of temperature according to conditions determined by user, and in which may be located:
 a. said growth chamber (10),
 b. said sampling chamber (11),
 c. upstream gate (3) defining the beginning of said growth chamber (10),
 d. downstream gate (4) defining the end of said growth chamber (10) and the beginning of said sampling chamber (11)
 e. second downstream gate (5) defining the end of said sampling chamber (11),
 f. turbidimeter (6) allowing the user or automated control system to monitor optical density of growing culture and to operate a feedback control system (13), allowing controlled movement of the tubing (1) on the basis of culture density (turbidostat function),
 g. one or several agitators (9).
It should be noted that the device elements listed in a-g may also be located outside of, or in the absence of, a thermostatically controlled box.
(7) represents the fresh medium in unused flexible tubing,
(8) represents a barrel loaded with fresh medium filled tubing, in order to dispense said fresh medium and tubing during operations.
(12) represents optional ultra-violet radiation gates,
(13) represents the control system that can consist of a computer connected with means of communication to different monitoring or operating interfaces, like optical density turbidimeters, temperature measurement and regulation devices, agitators and tilting motors, etc, that allow automation and control of operations, (14) represents the optional disposal barrel on which to wind up tubing containing disposed grown culture filled tubing, (15) represents disposed grown culture located downstream of said sampling chamber.

One potential configuration for the present device is shown in FIG. 1, as it appears after having been loaded with a fresh tube of sterile medium (shown divided into regions A-H by said gates (3), (4) and (5)).

Figure 4:
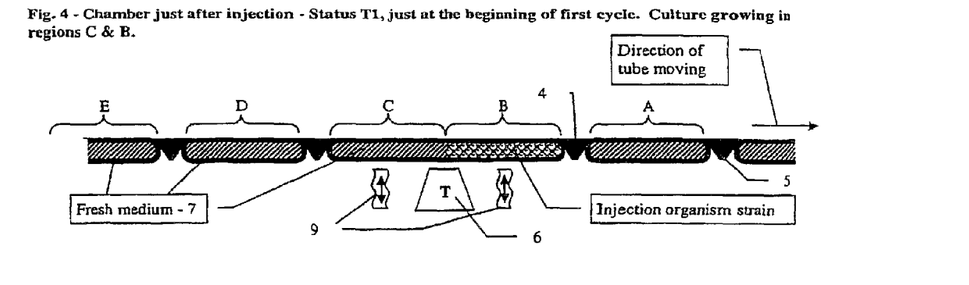
FIG. 4 symbolizes status T1 of said flexible tubing just after injection of cell strain.
Figure 5:
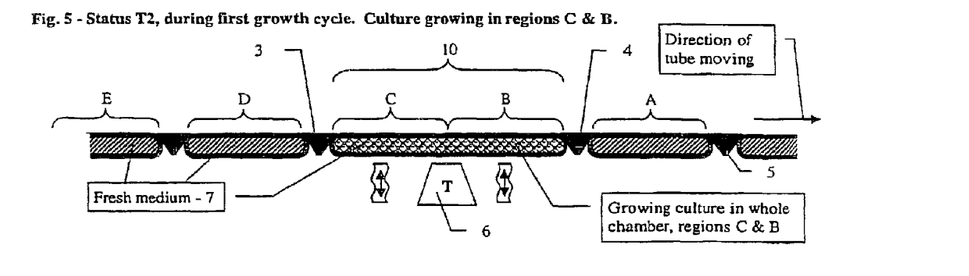
FIG. 5 symbolizes status T2 of the device which is a growing period during which the culture grows in the region defined as the growth chamber (10) limited by said gates (3) and (4).

Inoculation of the device with the chosen cell could be achieved by introduction of the cell into the growth chamber (FIG. 3), through injection (FIG. 4, region B). The culture would then be allowed to grow to the desired density and continuous culture would begin (FIG. 5).

Continuous culture would proceed by repetitive movements of the gated regions of tubing. This involves simultaneous movements of the gates, the tubing, the medium, and any culture within the tubing. The tubing will always move in the same direction; unused tubing containing fresh medium (and hereafter said to be 'upstream' of the growth chamber (7)) will move into the growth chamber and mix with the culture remaining there, providing the substrate for further growth of the cells contained therein. Before introduction into the growth chamber region, this medium and its associated tubing will be maintained in a sterile condition by separation from the growth chamber by the upstream gates (3). Used tubing containing grown culture will simultaneously be moved 'downstream' and separated from the growth chamber by the downstream gates (4).

When one or more growth chambers are present, the growth chambers may be used for the same or different purpose. For example, living cells could be grown in a first growth chamber and a second growth chamber with the same or different conditions. In one embodiment, a first growth chamber can be used to grow cells and a second growth chamber may then be used to treat the living cells under different conditions. For example, the cells may be treated to induce the expression of a desired product. Components or additives of the culture medium itself may be added prior to or after the culture begins. For example, all components or additives could be included in the media before beginning the culture, or components can be injected into one or more of the growth chambers after the culture has been initiated.

Figure 10:
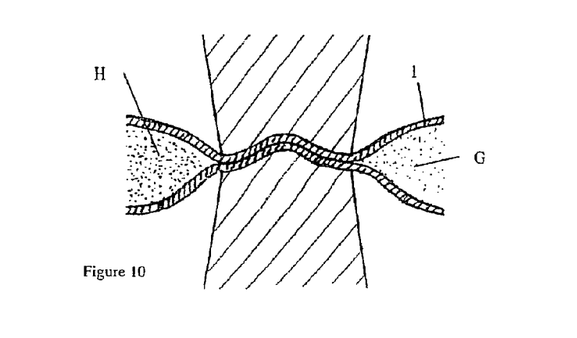
FIG. 10 displays a possible profile of teeth determining a gate in the configuration which consists of two stacking teeth pinching flexible tubing. Gates could also be determined by single teeth pressing against a moveable belt, removable clamps, or other mechanisms that prevent movement of cells through the gate and which can be alternately placed and removed in variable positions along the tubing.

Gate configuration is not a specific point of the present patent application. For example, in a given configuration, gates can be designed through one chain of multiple teeth simultaneously moved or in another configuration separated in distinct synchronized chains as depicted in FIG. 1. Gates can consist of a system made of two teeth pinching the tubing in a stacking manner as described in FIG. 10, avoiding contamination between regions G and H of the tubing through the precision of the interface between the teeth. In another configuration, sterile gates can be obtained by pressing one tooth against one side of the tubing and thereby pressing the tubing tightly against a fixed chassis along which tubing is slid during its peristaltic movement, as sketched in FIGS. 3 to 9, marks 3, 4 and 5.

Said thermostatically controlled box (2) is obtained by already known means such as a thermometer coupled with a heating and cooling device.

Aeration (gas exchange), when required for growth of the cultured cell or by the design of the experiment, is achieved directly and without mechanical assistance by the use of gas permeable tubing. For example and without being limiting, flexible gas permeable tubing can be made of silicone. Aeration could be achieved through exchange with the ambient atmosphere or through exchange with an artificially defined atmosphere (liquid or gas) that contacts the growth chamber or the entire chemostat. When an experiment demands anaerobiosis the flexible tubing can be gas impermeable. For example and without being limiting, flexible gas impermeable tubing can be made of coated or treated silicone.

For anaerobic evolution conditions, regions of the tubing can also be confined in a specific and controlled atmospheric area to control gas exchange dynamics. This can be achieved either by making said thermostatically controlled box gastight and then injecting neutral gas into it or by placing the complete device in an atmosphere controlled room.

Counter-selection of static variants is achieved by replacement of the growth chamber surface along with growth medium.

Figure 2:
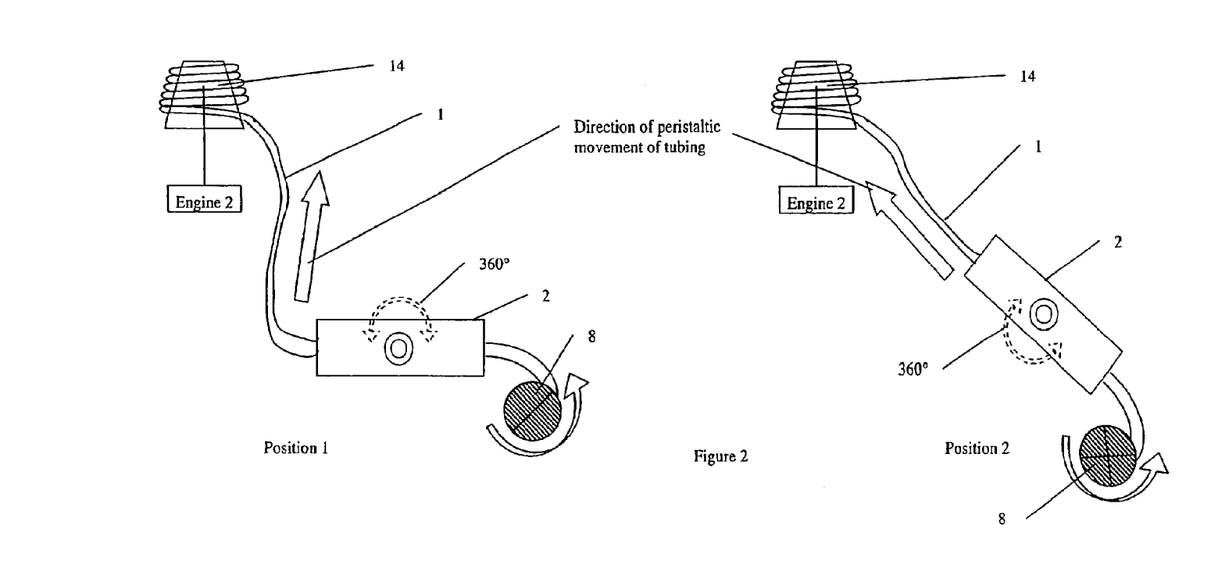
FIG. 2 displays two possible positions of the device, exemplifying the fact that said thermostatically controlled box (2) and other pieces of said device associated with said culture chamber can be tilted to various degrees for agitation purposes, gas circulation and removal purposes, and purposes of guaranteeing the removal of granulated (aggregated) cells that might escape dilution by settling to the bottom.
Figure 3:
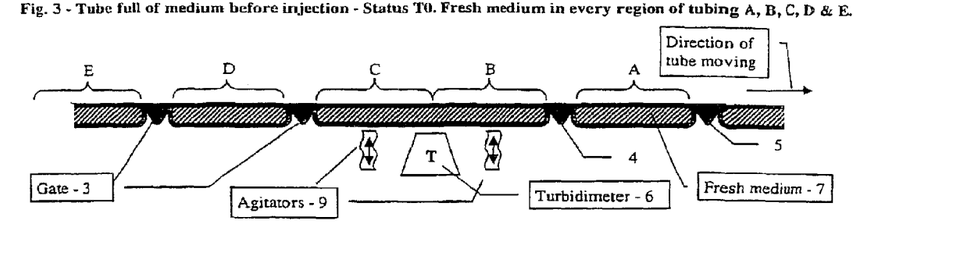
FIG. 3 symbolizes status T0 of the device in which all regions of said flexible tubing are filled with fresh medium before injection of the cell intended for continuous culture.

The device is further designed to be operable in a variety of orientations with respect to gravity, that is, to be tilted as shown by FIG. 2, along a range of up to 360°.

Dilution-resistant variants may avoid dilution by sticking to one another, rather than to the chamber wall if aggregated cells can fall upstream and thereby avoid removal from the chamber. Hence it is desirable that the tubing generally be tilted downward, such that aggregated cells will fall toward the region that will be removed from the growth chamber during a cycle of tube movement. This configuration involves tilting the device so that the downstream gates are below the upstream gates with respect to gravity.

The growing chamber can be depressurized or over pressurized according to conditions chosen by the experimenter. Different ways of adjusting pressure can be used, for instance applying vacuum or pressurized air to the fresh medium and tubing through its upstream extremity and across the growth chamber; another way of depressurizing or overpressurizing tubing can be done by alternate pinching and locking tubing upstream of or inside the growth chamber.

Figure 6:
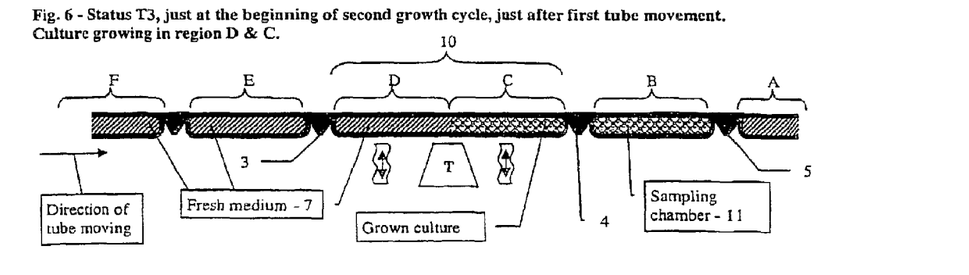
FIG. 6 symbolizes status T3 of device, just after the first peristaltic movement of tubing and associated medium, which determines the beginning of the second growing cycle, introducing fresh tubing and medium through movement of gate 3 simultaneous with a transfer of equivalent volume of tubing, medium, and grown culture out of the growth chamber region (10) and into the sampling chamber region (11) by movement of gate 4. It is critical to recognize that the tubing, the medium that is within the tubing, and any culture that has grown in that medium, all move together. Fluid transfer only occurs insofar as fresh medium and grown culture mix together through agitation within the growth chamber region.
Figure 7:
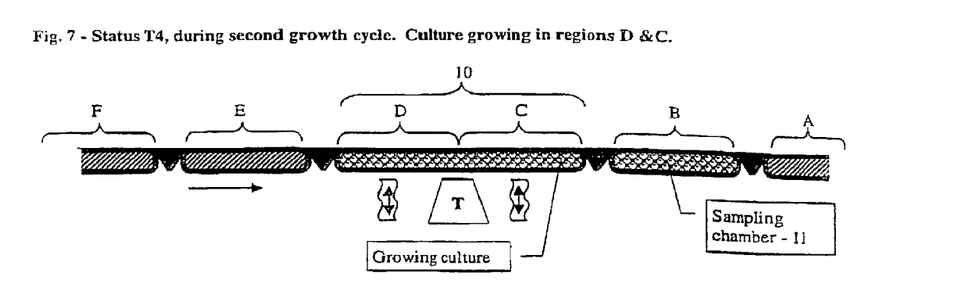
FIG. 7 symbolizes status T4 of the device which is the second growing cycle; during this cycle cells that remain in the growth chamber after peristaltic movement of the tubing can now grow using nutrients provided in the fresh medium that is mixed with the remaining culture during this step.
Figure 8:
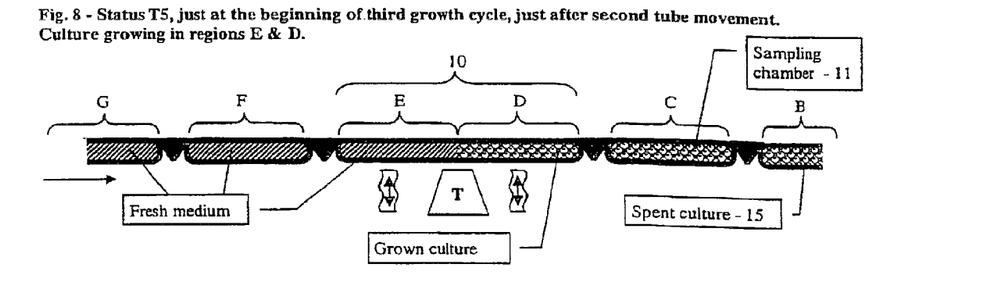
FIG. 8 symbolizes status T5 of device, just after the second peristaltic movement of the tubing and the contained medium, which determines the beginning of the third growing cycle, introducing fresh tubing and medium through movement of gate 3 simultaneous with a transfer of equivalent volume of tubing, medium, and grown culture out of the growth chamber region (10) and into the sampling chamber region (11) by movement of gate 4.
Figure 9:
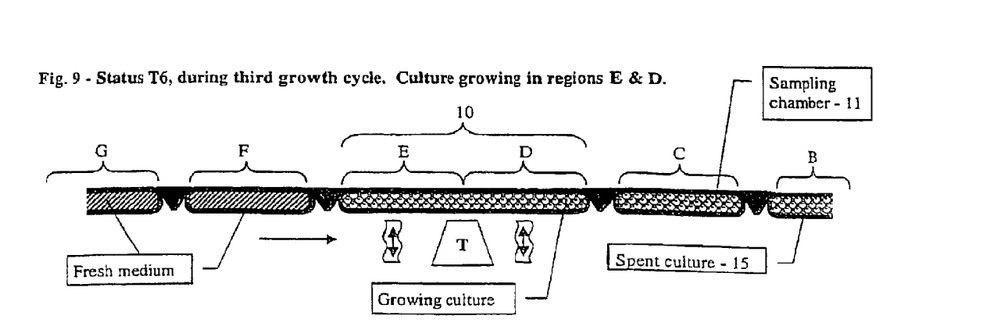
FIG. 9 symbolizes status T6 of device which is the third growing cycle; this step is equivalent to status T4 and indicates the repetitive nature of further operations. Samples of selected cells may be removed at any time from the sampling chamber region (11) using a syringe or other retrieval device.

When the medium is contained in gas permeable tubing, air bubbles may form within the medium. These will rise to the top of a sealed region of tubing and become trapped there until the movement of the region (and the gates defining it) releases the region into either the growth chamber, the sampling chamber or the endpoint of the chemostat (FIG. 6, regions D-C, B or A, respectively). If the device is tilted downward such bubbles will accumulate in the growth chamber or sampling chamber and displace the culture. The device is designed to periodically tilt upward for a cycle of the tube movement, allowing for the removal of accumulated gas from said chambers.

Tilting movements of the device, and/or shaking of the growth chamber by an external device (9) can be used to decrease aggregation of cells within the growth chamber. Alternatively, one or several stirring bars can be included in the tubing filled with fresh medium before sterilization and magnetically agitated during culture operations.

The proportional length of the regions of fresh medium defined by the upstream gates as compared to the length of the culture chamber will define the degree of dilution achieved during a cycle.

The frequency of dilution can be determined either by timing (chemostat function) or by feedback regulation whereby the density of the culture in the growth chamber is measured by a turbidimeter (FIG. 1—mark 6) and the dilution cycle occurs when the turbidity reaches a threshold value (turbidostat function).

The sampling chamber allows withdrawing grown culture in order to analyze the outcome of an experiment, collect cells with improved growth rate for further culture, storage, or functional implementation, or other purposes such as counting the population, checking the chemical composition of the medium, or testing the pH of grown culture. In order to achieve permanent monitoring of pH inside growth chamber, tubing can include by construction a pH indicator line embedded/encrusted in the wall of the tubing.

Any form of liquid or semi-solid material can be used as a growth medium in the present device. The ability to utilize semi-solid growth substrates is a notable advancement over prior art. The growth medium, which will define the metabolic processes improved by the selection process, can be chosen and defined by the user.

If needed, this device can contain multiple growth chambers, such that the downstream gates of one growth chamber become the upstream gates of another. This could, for example, allow one cell to grow alone in the first chamber, and then act as the source of nutrition for a second cell (or virus) in the second chamber.

The invention may be used to produce a preparation, such as a biologic for a drug, a vaccine, or an antitoxin, that is synthesized from cells grown by the invention or their products. The biologic may be used as a diagnostic, preventive, or therapeutic agent. For example, the present invention may be used to produce therapeutic proteins such as insulin.

In a preferred embodiment, the device and/or method may be cycled in a manner to continually collect stem cells in their undifferentiated state. Furthermore, the culture conditions may be modified to inhibit the differentiation of the stem cells. For example, stem cell differentiation inhibitors (e.g., inhibitors of aldehyde dehydrogenase, inhibitors of phosphoinositide 3-kinase, TGF Receptor Kinase inhibitors, TGF-B Receptor Kinase Inhibitor etc. . . . ) may be added to the culture medium. Alternatively, process conditions such as the amount of oxygen delivered to the culture medium may be increased or decreased to improve the growth of certain stem cells and/or slow down or improve differentiation of the stem cells.

As some cells require a substrate to grow, a physical support or structure can be added to the vessel culture chamber. In a preferred embodiment, a continuous support could be added inside the tubing like a continuous fiber bed, constituted by a thin continuous fiber like support structure, can be added to the vessel culture chamber which could let cells grow in 3 dimensions. For example, the support could be a fiber bed, which provides support for the growth of cells such as stem cells, plants cells and other types of cells that prefer such a support structure, and in some specific conditions or change of conditions, to process the natural selection for targeted mutations.

In a preferred embodiment, a fibrous material as described in Huang et al., Continuous Production of butanol by Clostridium acetobutylicum immobilized in a fibrous bed reactor, Appl Biochem Biotechnol. 2004 Spring; 113-116: 887-98, incorporated by reference herein. The structure and size of the tubing may also be varied to avoid the need for incorporating a support structure into the mobile vessel culture chamber. In a preferred embodiment, tubing with a smaller diameter is used so the cells may adhere in a more natural manner.

This device and method allows researchers and product developers to evolve any strain of culturable living cells in suspension or any strain of culturable living cells which are not in suspension which grow on the wall of the tubing or on a support which could be a fiber bed in the tubing through sustained growth (continuous culture); the resulting improved cell can constitute a new strain or species. These new cells can be identified by mutations acquired during the course of culture, and these mutations may allow the new cells to be distinguished from their ancestors' genotype characteristics. This device and method allow the researcher to select new strains of any living cell by segregating individuals with improved rates of reproduction through the process of natural selection. The invention also provides an improved and completely distinct method and device for continuous culture of cells such as yeast, plant cells, animal cells or stem cells.

In a further embodiment, an emitter can be used to subject the cells, permanently or temporarily, to at least one of radio waves, light waves, x-rays, sound waves, an electro magnetic field, a radioactive field, radioactive media, or combinations thereof. The following publications are incorporated by reference: *Biofizika.* 2005 July-August, 50(4):689-92; *Bioelectromagnetics.* 2005 September, 26(6):431-9; *Chem Commun (Camb).* 2005 Jan. 14, (2):174-6; *Biophys J.* 2005 Februray, 88(2):1496-9; *Bioelectromagnetics.* 1981, 2(3): 285-9; *Sb Lek.* 1998, 99(4):455-64; *Antimicrob Agents Chemother.* 2004 December, 48(12):4662-4; *J Food Prot.* 2003 September, 66(9):1712-5; *Astrobiology.* 2006 April, 6(2):332-47; *Life Sci Space Res.* 1970, 8:33-8; *Adv Space Res.* 1995 March, 15(3):211-4; *Radiat Res.* 2006 May, 165(5):532-7; *Mutagenesis.* 2004 September, 19(5):349-54; *Cancer Sci.* 2006 June, 97(6):535-9; *Appl Environ Microbiol.* 2006 May, 72(5):3608-14; and *Pol J. Microbial.* 2005, 54 Suppl:7-11.

In another embodiment, the growth chamber region of the device could be subjected to, permanently or temporarily, subjecting the cells to a different gravitational force. For example, the cells can be grown in a microgravity environment. The following publications are incorporated by reference: *J Gravit Physiol.* 2004 March; 11(1):75-80; *Immunol Rev.* 2005 December; 208:267-80; and *J Gravit Physiol.* 2004 July; 11(2):P181-3.

Modifications and variations of the present invention relating to the apparatus and method will be obvious to those skilled in the art from the foregoing detailed description of the invention. Such modifications and variations are intended to come within the scope of the appended claims.

What is claimed is:

1. A method for growing cells that are not in suspension, comprising:
  a) providing flexible tubing containing culture medium, and a surface on which living cells can grow in said tubing, the surface being at least one of (i) the inner surface of the tubing, the diameter of the tubing being small so that the living cells may adhere in a natural manner or (ii) a continuous fiber inserted inside the tubing, and a system of gates achieved by clamps, each of the gates being capable of open and closed positions, the gates being positioned so as to be able to divide the tubing into:
  i) an upstream region containing unused culture medium and a portion of the surface which is unused on which the living cells can grow;
  ii) a downstream region containing spent culture medium; and
  iii) a growth chamber region for growing said cells on the surface, the growth chamber region being disposed between the upstream and downstream regions; and
  b) closing selected ones of the gates on the tubing to define the growth chamber region of the tubing between the upstream and downstream regions of the tubing, and introducing viable cells into the growth chamber region;
  c) cyclically closing and opening selected ones of the gates to redefine the growth chamber region of the tubing so that a first portion of the previously defined growth chamber region becomes a portion of the downstream region of the tubing, and a portion of the previously defined upstream region of the tubing becomes a portion of the growth chamber region of the tubing and provides the surface for further growth of the living cells; and
  d) repeating step c) until a desired amount of said living cells have grown;
  wherein the growth chamber region is subjected to a pre-determined growth condition, and the repetition of step c) selects for those of the living cells that demonstrate an improved rate of reproduction responsive to said growth condition;
  wherein the tubing including the medium, the surface and culture inside the tubing move through a simultaneous movement of the system of gates to cyclically redefine the growth chamber region of the tubing; and
  wherein the living cells are cells that do not grow in suspension.

2. The method of claim 1, further comprising a step of providing a control system that measures culture density in the growth chamber, and controls the step of cyclically closing and opening selected ones of the gates based on the measured culture density at any time prior to step c) or step d).

3. The method according to claim 2, comprising the further step of withdrawing a sample of said living cells from said spent culture medium from the downstream region at any time after step c) or step d).

4. The method according to claim 2, further comprising isolating said living cells from the downstream region at any time after step c) or step d).

5. The method according to claim 2, wherein the living cells are selected from the group consisting of yeast cells, animal cells, plant cells, and stem cells.

6. The method according to claim 2, wherein the living cells are stem cells.

7. The method according to claim 6, wherein the stem cells are selected from the group consisting of hematopoietic stem cells, bone marrow stem cells, stromal cells, astrocytes, oligidendrocytes, embryonic stem cells, fetal stem cells, umbilical cord stem cells, placenta derived stem cells, and adult stem cells.

8. The method according to claim 7, wherein the stem cells are selected from the group consisting of hematopoietic stem cells, bone marrow stem cells, stromal cells, astrocytes and oligidendrocytes.

9. The method according to claim 1, wherein the surface in which the cells are grown is the inner surface of the tubing.

10. The method according to claim 1, wherein the surface in which the cells are grown is the continuous fiber.

11. The method according to claim 2, wherein the growth chamber region comprises one or more growth chambers.

12. The method according to claim 2, wherein one or more types of cells are grown in the growth chamber region.

13. The method according to claim 2, wherein the desired amount of said living cells of step d) is defined as a pre-determined density level of the cells.

14. The method according to claim 2, wherein the tubing is gas permeable.

15. The method according to claim 2, wherein the tubing is gas impermeable.

16. The method according to claim 2, wherein the tubing is one of transparent or translucent, a turbidimeter being used to determine the density level of the cells.

17. The method according to claim 2, wherein the control system further regulates the pressure of the growth chamber region of the tubing relative to ambient pressure to establish the pre-determined growth condition, responsive to which the living cells are subjected to selection for those that demonstrate the improved rate of reproduction.

18. The method according to claim 2, further comprising measuring a pH of the culture medium in the growth chamber region at any time after step a).

19. The method according to claim 2, wherein the control system further regulates the temperature of the growth chamber region with a temperature regulator constructed to control the temperature of the growth chamber region of the tubing to establish the pre-determined growth condition, responsive to which the living cells are subjected to selection for those that demonstrate the improved rate of reproduction.

20. The method according to claim 2, wherein the control system further agitates the culture medium in the growth chamber region with an agitator.

21. The method according to claim 2, wherein the control system further reduces aggregation of cells by tilting the tubing so that downstream gates are below upstream gates with respect to gravity such that aggregated cells fall toward a region that will be removed from the growth chamber during a cycle of tube movement.

* * * * *